United States Patent [19]

Landauer

[11] 4,169,852
[45] Oct. 2, 1979

[54] PROCESS FOR THE PREPARATION OF N-(CHLOROARYL)-N',N'-DIALKYLAMIDINES

[75] Inventor: Franz Landauer, Frankfurt am Main, Fed. Rep. of Germany

[73] Assignee: Hoechst Aktiengesellschaft, Frankfurt am Main, Fed. Rep. of Germany

[21] Appl. No.: 566,401

[22] Filed: Apr. 9, 1975

[30] Foreign Application Priority Data

Apr. 11, 1974 [DE] Fed. Rep. of Germany ....... 2417669

[51] Int. Cl.² ............................................ C07C 123/00
[52] U.S. Cl. .............................................. 260/564 RF
[58] Field of Search ................................... 260/564 RF

[56] References Cited

U.S. PATENT DOCUMENTS 3,911,012 10/1975 Krieger .......................... 260/564 RF Primary Examiner—Gerald A. Schwartz
Attorney, Agent, or Firm—Curtis, Morris & Safford

[57] ABSTRACT

A process for the preparation of N-(chloroaryl)-N',N'-dialkylamidines in which N-aryl-N',N'-dialkylamidines in the form of their salts are directly chlorinated in halogenated hydrocarbons at 15°–80° C. From the hydrochloride salts thus obtained the free amidines are set free with alkaline agents. The N-(chloroaryl)-N',N'-dialkylamidines are valuable intermediates for the preparation of dyestuffs and insecticides.

4 Claims, No Drawings

PROCESS FOR THE PREPARATION OF N-(CHLOROARYL)-N',N'-DIALKYLAMIDINES

This invention relates to a process for the preparation of N-(chloroaryl)-N',N'-dialkylamidines.

It is already known (cf. Chem. Ber. 92,837 (1959); DT-PS No. 1,542,715), that, starting from N,N-dialkylamides such as, for example, N,N-dialkylformamide and aromatic amines with, for example, phosphoroxychloride it is possible to prepare the corresponding N-aryl-N',N'-dialkyl-formamidines. These amidines can also be prepared out of arylisocyanates and dialkylamides (cf U.S. Pat. No. 3,284,289). In these reactions the aromatic radicals can also be substituted, such as, for example, they can be halogenated. These known processes of preparation for amidines halogenated, especially chlorinated on the nucleus have the big disadvantage that they must always start from chlorinated aromatic amines. But the latter are only accessible via several reaction steps which are partially very expensive. N-(2-methyl-4-chlorophenyl)-N',N'-dimethyl-formamidine may, for example, be obtained according to the following reaction scheme:

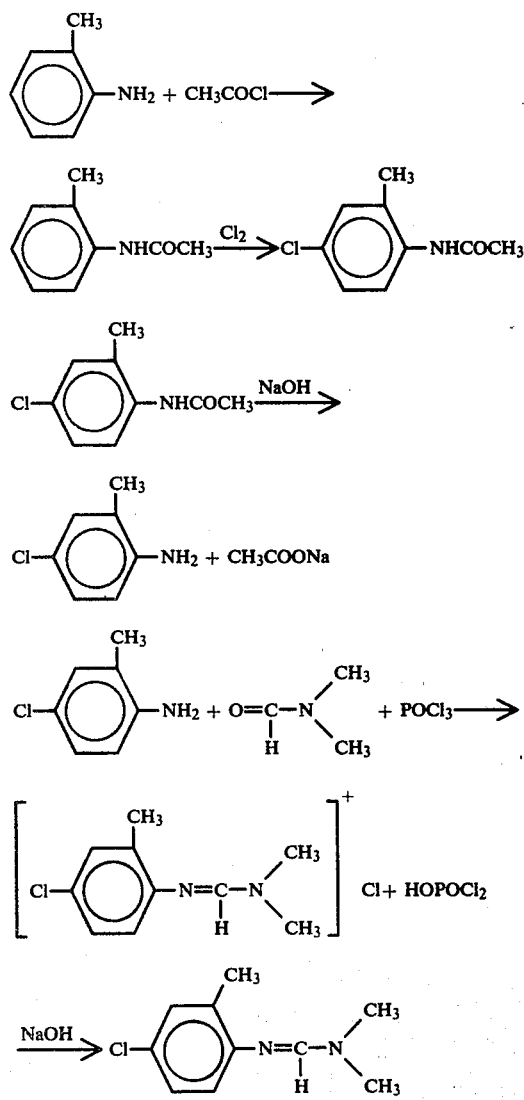

This scheme shows that already 3 separately running reactions are necessary only for the preparation of the chlorinated amine. For this purpose individual reactors are needed in each case and the reactions need much time and energy.

It has now been found that chlorinated N-aryl-N',N'-dialkylamidine or their salts can be prepared in an easy way, by chlorinating N-aryl-N',N'-dialkylamidine of the general formula I in form of its salts

in which $R^1$ represents a phenyl or naphthyl radical which can be substituted by eventually further substituted phenyl, naphthyl or lower alkyl groups whereby these substituents are bound directly or by means of an oxygen, sulfur or nitrogen atom; $R^2$ represents a lower molecular aliphatic radical, or preferably a hydrogen atom; $R^3$ and $R^4$ stand for identic or different aliphatic radicals having up to 8 carbon atoms, in halogenated hydrocarbons at temperatures of about 15°–80° C. and setting the amidines eventually free with the aid of bases.

Preference is given to starting materials of the formula I, in which $R_1$ represents a phenyl or naphthyl radical which can be substituted by one or more phenyl, phenoxy, phenyl-sulfone, lower alkyl, lower haloalkyl or lower alkoxy radicals, $R^2$ represents a hydrogen atom and $R^3$ and $R^4$ represent lower alkyl groups.

The process of the invention is effected in the following way: N,N-dialkylamide of the formula II

in which $R^2$, $R^3$ and $R^4$ have the above mentioned significations, reacts firstly with an acid condensating agent, for example, with phosphoroxychloride in chlorhydrocarbon to obtain an N,N-dialkylamide-phosphoroxychloride adduct; the desired aromatic amine of the formula III

in which $R^1$ has the above-mentioned signification is added and after reaction the chlorination is effected. The salts of the N-aryl-N',N'-dialkylamidines obtained by this reaction are chlorinated directly afterwards; it is not necessary to isolate the free N-aryl-N',N'-dialkylamides from the salt.

According to the invention, the following amines of the formula III can be used: o-trifluoromethylaniline, ansidine, naphthylamine, p-phenoxyaniline, p-aminodiphenyl or p-amino-siphenylsulfone. Preference is given to aniline and o-toluidine.

As dialkylamides of the formula II there are used, for example: N,N-diethylacetamide, N,N-dimethyl-priopionamide, N,N-di-n-amylformamide, N,N-di-n-hexyl-formamide or N,N-di-isobutylformamide. Preference is given to dimethylformamide.

As acid condensation agents phsophoroxychloride, dichlorophosphoric acid, sulfurylchloride etc. are used as usual.

According to the invention halogenhydrocarbons, preferably chlorhydrocarbons or fluorhydrocarbons are used as solvents, respectively as suspension agents. As chlorhydrocarbons may be cited, for example:

chloroform, tetrachloroethane, dichlorobenzene such as, for example, o-dichlorobenzene, preferably carbontetrachloride and chlorobenzene. It goes without saying that also mixtures of these chlorohydrocarbons can be used, eventually even a mixture with other halogenated hydrocarbons. The reaction can be effected with the aid of a suitable apparatus in continous as well as in a discontinous way, without pressure or under elevated pressure. When chlorinating, the chlorine can be brought onto the surface of the well stirred liquid, but preferably directly into the liquid. If the chlorinated end-product should contain only one chlorine atom in the aromatic radical it may be suitable to use not more than 1.2 mol of chlorine, preferably 0.74-1 mol of chlorine per mol of amidine. It goes without saying that also less than 0.75 mol of chlorine may be used; in this case the amount of the non chlorinated amidine, eventually to be reconducted, is higher.

The process of the invention has the advantage that the multitude of reaction steps necessary for the protection of the amino group when chlorinating are superflous, as surprisingly, the salts of the N-aryl-N',N'-dialkylamidine are chlorinated. This means in a technically easy one-pot process, starting from aromatic amines unchlorinated, in the aryl radical, the corresponding N',N'-dialkylamidines, respectively salts therefrom can be prepared in the usual way; they can be chlorinated without isolation in the same apparatus. The free amidine can subsequently be obtained in the usual way from the salts by alkaline decomposition.

The reaction temperature varies between 15° and 80° C., preferably between 25° and 50° C. Eventually, halogenating catalysts such as ferric chloride may be added.

According to known methods, the free amidines can then be obtained from the salts of the chlorinated amidines by means of inorganic or organic bases.

The N-(chloroaryl)-N',N'-dialkylamidine obtained according to the process of the invention are valuable intermediate products for the preparation of dyestuffs and insecticides.

The following examples illustrate the invention.

EXAMPLE 1

Reaction of an amidine hydrochloride:

To a mixture of 67 g of N-(2-methylphenyl)-N',N'-dimethylformamidine and 800 g of chlorobenzene 30 g of hydrochloric acid gas were added under stirring at 20°-30° C. and subsequently, at 38°-42° C., 30 g of chlorine gas in the course of one hour. After chlorination the hydrochloric acid gas is blown out at 40°-45° C. by means of nitrogen. The free formamidine is then prepared from the hydrochloride with a 15% sodium hydroxide solution. After separation of the organic phase and after separation by distillation of the chlorobenzene the crude formamidine was distilled in vacuo in fractions.

34 g of N-(2-methyl-4-chlorophenyl)-N',N'-dimethylformamidine and 29 g of N-(2-methyl-phenyl)-N',N'-dimethylformamidine were recovered. The same yield was obtained when the chlorine was added at 13°-16° C.

EXAMPLE 2

Reaction after the preparation of amidine (crude amidine salt as starting material:

To a solution of 74 g of dimethylformamide in 0.5 l of waterfree chlorobenzene 154 g of phosphoroxychloride were added dropwise under stirring, in the course of 40 minutes; afterwards, 107 g of o-toluidine were added in the course of 20 minutes. Stirring of the reaction mixture was continued at 65° C. during 2 hours. After cooling to 30°-35° C. 57 g of chlorine were added at this temperature in the course of about 2 hours. After chlorination the mixture is cooled down to 0°-5° C. and adjusted to a pH value of 11 by adding a sodium hydroxide solution at 33%. The organic phase is then separated and dried over sodium sulfate. The chlorobenzene was then distilled off under reduced pressure. The crude formamidine was then distilled in vacuo in fractions. Apart from 65 g of N-(2-methyl-phenyl)-N',N'-dimethyl-formamidine 80 g of N-(2-methyl-4-chlorophenyl)-N',N'-dimethyl-formamidine were obtained.

The same products with about an equal yield were obtained when using for the condensation 135 g of sulfurylchloride instead of 154 g of phosphoroxychloride.

EXAMPLE 3

Chlorine was added at 30° C. under vigourous stirring to 81 g of N-(2-methylphenyl)-N',N'-dimethyl-formamidine dissolved in 800 ml of chlorobenzene. Shortly after the beginning of the chlorination the clear solution becomes turbid by the formation of the hydrochloride. In the course of one hour 30 g of chlorine gas were introduced in total. After the chlorination the pH value was adjusted to 10-11 by adding under cooling of a potassium hydroxide solution at 50%. After separation of the organic phase the chlorbenzene is distilled off in vacuo; afterwarde the crude amidine-mixture is distilled off. 59 g of N-(2-methyl-4-chlorophenyl)-N',N'-dimethylformamidine were obtained as well as 14.5 g of N-(2-methylphenyl)-N',N'-dimethyl-formamidine.

The same yield is obtained when using the same amount of carbontetrachloride instead of chlorobenzene.

EXAMPLE 4

162 g of N-(2-methylphenyl)-N',N'-dimethylformamidine were dissolved in 440 g of chlorobenzene. Hydrochloric acid gas was introduced at 20°-40° C. until the solution has absorbed 37 g. Subsequently 85 g of chlorine gas were added in the course of 1.5 hours at 50° C. to the reaction mixture. After separation of the sodium chloride solution the organic phase was dried over sodium sulfate and distilled off in vacuo, whereby at first the chlorobenzene, afterwards the N-(2-methyl-4-chlorophenyl)-N',N'-dimethyl-formamidine mixed with some N-(2-methyl-6-choloropheny1)-N',N'-dimethyl-formamidine distilled off. By rectification this formamidine mixture can be purified.

Yield: 155 g of N-(2-methyl-4-chlorophenyl)-N',N'-dimethylformamidine, i.e. 79% of the theoretical yield.

I claim:

1. A process for the preparation of an N-(chloroaryl)-N',N'-dialkylamidine which comprises reacting, in a halogenated hydrocarbon, an N',N'-dialkylamide of the formula

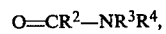

$O=CR^2-NR^3R^4$, wherein $R^2$ is hydrogen or a lower aliphatic radical and each of $R^3$ and $R^4$ is an aliphatic radical of up to 8 carbon atoms, with an acid condensing agent to form the adduct thereof, reacting said adduct with an amine of the formula $$R^1-NH_2,$$

wherein $R^1$ is (a) phenyl or (b) naphthyl, or (a) phenyl or (b) naphthyl substituted by phenyl, naphthyl or lower alkyl or substituted phenyl, naphthyl or lower alkyl, said substituents in (a) or (b) being bound directly or by means of an oxygen, sulfur or nitrogen atom, and chlorinating, without prior isolation, the reaction product of the formula

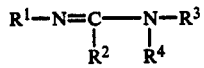

at a temperature of about 15° to 80° C.

2. The process as defined in claim 1, wherein $R^1$ is phenyl or naphthyl, or phenyl or naphthyl substituted by phenyl, phenoxy, phenylsulfone, lower alkyl, lower haloalkyl, or lower alkoxy, $R^2$ is hydrogen or lower alkyl, and each of $R^3$ and $R^4$ is lower alkyl.

3. The process as defined in claim 1, wherein the chlorination temperature is from 25° to 50° C.

4. The process as defined in claim 1, wherein the chlorination is effected with chlorine.

* * * * *